United States Patent
Sippio

(10) Patent No.: US 8,574,208 B1
(45) Date of Patent: Nov. 5, 2013

(54) DISPOSABLE WASTE BAG

(76) Inventor: Linda Sippio, Miami, FL (US)

( * ) Notice: Subject to any disclaimer, the term of this patent is extended or adjusted under 35 U.S.C. 154(b) by 1498 days.

(21) Appl. No.: 12/024,751

(22) Filed: Feb. 1, 2008

(51) Int. Cl.
*A61F 5/44* (2006.01)

(52) U.S. Cl.
USPC .................................. 604/355; 604/385.03

(58) Field of Classification Search
USPC ................ 604/317, 327, 355, 348, 385.03; 600/574; 4/144.3
See application file for complete search history.

(56) References Cited

U.S. PATENT DOCUMENTS

| | | | | |
|---|---|---|---|---|
| 2,066,400 A | * | 1/1937 | Hale | 4/455 |
| 2,222,825 A | * | 11/1940 | Starck | 604/351 |
| 3,577,989 A | * | 5/1971 | Anderson | 604/348 |
| 4,031,897 A | * | 6/1977 | Graetz | 604/347 |
| 5,868,465 A | * | 2/1999 | Kvalvik | 297/253 |
| 6,602,233 B1 | | 8/2003 | Palumbo et al. | 604/355 |
| 2005/0275261 A1 | * | 12/2005 | Graupner et al. | 297/256.17 |
| 2010/0179497 A1 | * | 7/2010 | Brownlee | 604/385.14 |

* cited by examiner

*Primary Examiner* — Tatyana Zalukaeva
*Assistant Examiner* — Benedict L Hanrahan
(74) *Attorney, Agent, or Firm* — Jesus Sanchelima; Christian Sanchelima

(57) ABSTRACT

A disposable waste bag to be used in the management and collection of a user's urine and fecal matter in places where sanitary facilities do not exist or other situations that make the use of the present invention desirable. A sheet having a substantially truncated triangular shape having a front end and a larger rear side with two lateral rear ends. A rim with a narrow portion is cooperatively shaped to cover the user's genitalia. An enlarged portion of the rim covers the perianal area. The rim is slightly stiffer than the sheet member and extends symmetrically and longitudinally from the first end towards the rear side. The rim is preferably provided with a sealing adhesive to prevent the collected urine and feces from spilling out. A belt is used around a user's waist to keep the bag in place.

6 Claims, 4 Drawing Sheets

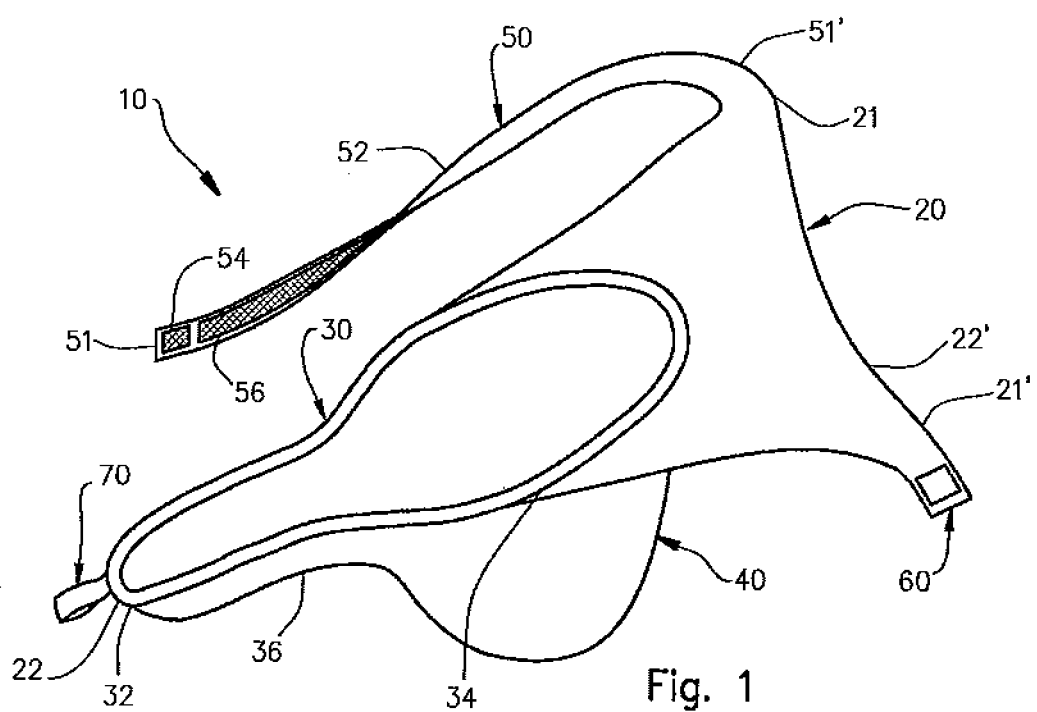
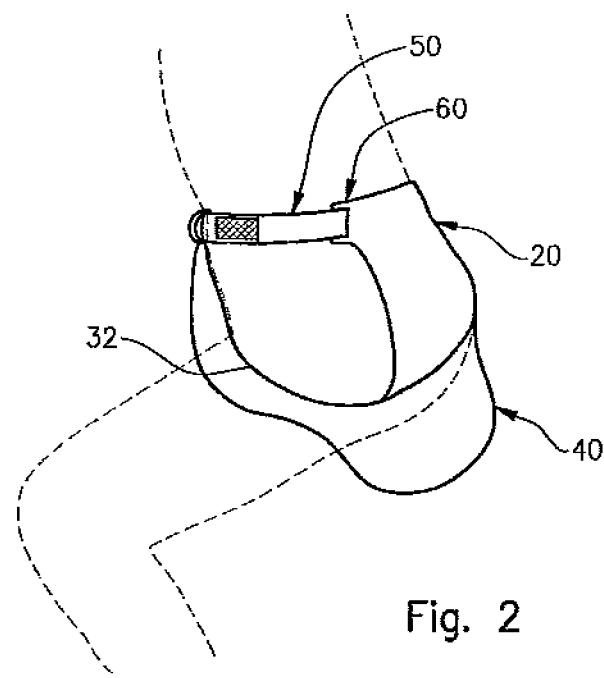

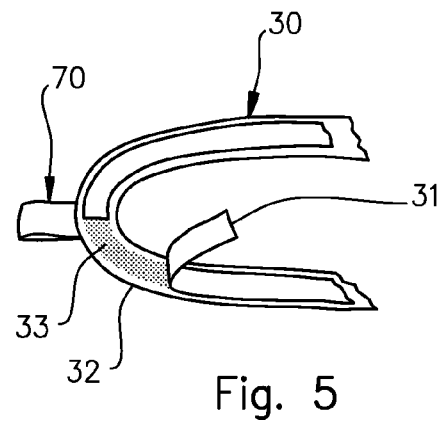
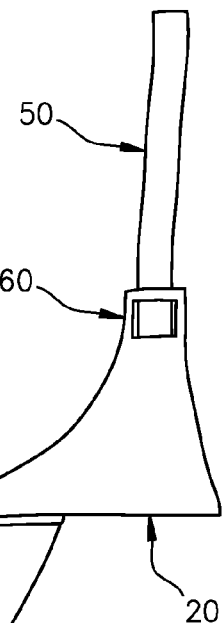
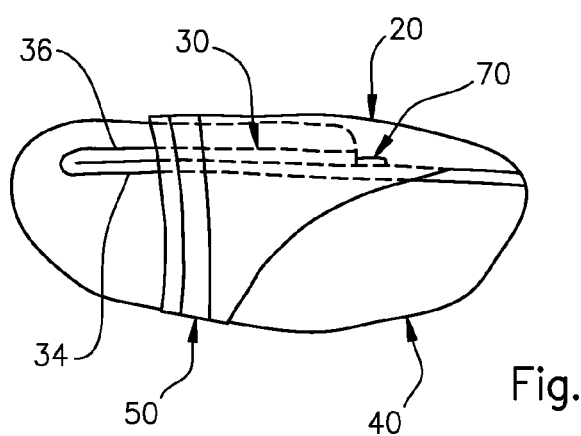

DISPOSABLE WASTE BAG

BACKGROUND OF THE INVENTION

1. Field of the Invention

The present invention relates to a disposable waste bag, and more particularly, to a disposable waste bag that is ergonomically compatible and volumetrically efficient that can be readily used and disposed of.

2. Description of the Related Art

The lack of availability of sanitary facilities at a given time makes this invention particularly desirable. For example, in combat zones, especially in urban areas where soldiers are suddenly deployed for long hours, the need to attend physiological acts cannot distract their alertness. Also, during natural disasters, or other equivalent situations, such as pandemic diseases where disposed of feces in a sanitary form is desired. Finding an appropriate place may not be possible. Thus, a simple device for collecting feces and urine without requiring the total immobilization of the user is quite desirable.

Several designs for a waste bag have been designed in the past. None of them, however, includes a disposable waste bag that permits a user to readily put on the bag to cover his/her genitals and excrete the feces substantially as if he/she were in a sanitary facility. The urine and feces, in the present invention, are collected and disposed of with minimal contact with a user.

Applicant believes that the closest reference corresponds to U.S. Pat. No. 6,602,233 issued to Palumbo et al. for an easy to place and detach adhesive fecal management collector on Aug. 5, 2003. However, it differs from the present invention because it requires the use of a diaper and adhesives that press bag 11 against a user's body, in essence teaching away from the present invention. Palumbo was concerned with mounting his collector to a user's body with adhesives and providing for lobes 13 and 14 for the detachment of the device. Col. 3, lines 3 through 5. The present invention relies on straps, like a belt, and a loop (with front) to support the bag in position. The liquid impermeable bag in this invention has a cooperative shape in the front that causes the urine to fall down to the bag's enlarged reservoir portion. The bag is kept loosely around the genitalia and perianal areas except the edges for readily retrieving and discarding the contents.

Other patents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide a disposable waste bag that is ergonomically compatible.

It is another object of this invention to provide a disposable waste bag that is volumetrically efficient.

It is still another object of the present invention to provide a disposable waste bag that includes an accessibly adjustable means of fastening and readily detaching the device.

It is still another object of the present invention to provide a disposable waste bag with accessible means of sealing the human waste content.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1 represents an isometric view of the present invention.

FIG. 2 shows a side elevational view of the present invention on a user (broken lines) while in use.

FIG. 5 is an enlarged detailed view of a portion of the rim of one of the preferred embodiments for sealing the contents after use.

FIG. 6 is a side elevational view of the present invention sealed for disposal.

FIG. 7 is a top elevational view of the embodiment shown in the previous figure sealed, wrapped, and prepared for disposal.

DETAILED DESCRIPTION OF THE PREFERRED EMBODIMENT

Figure 3:
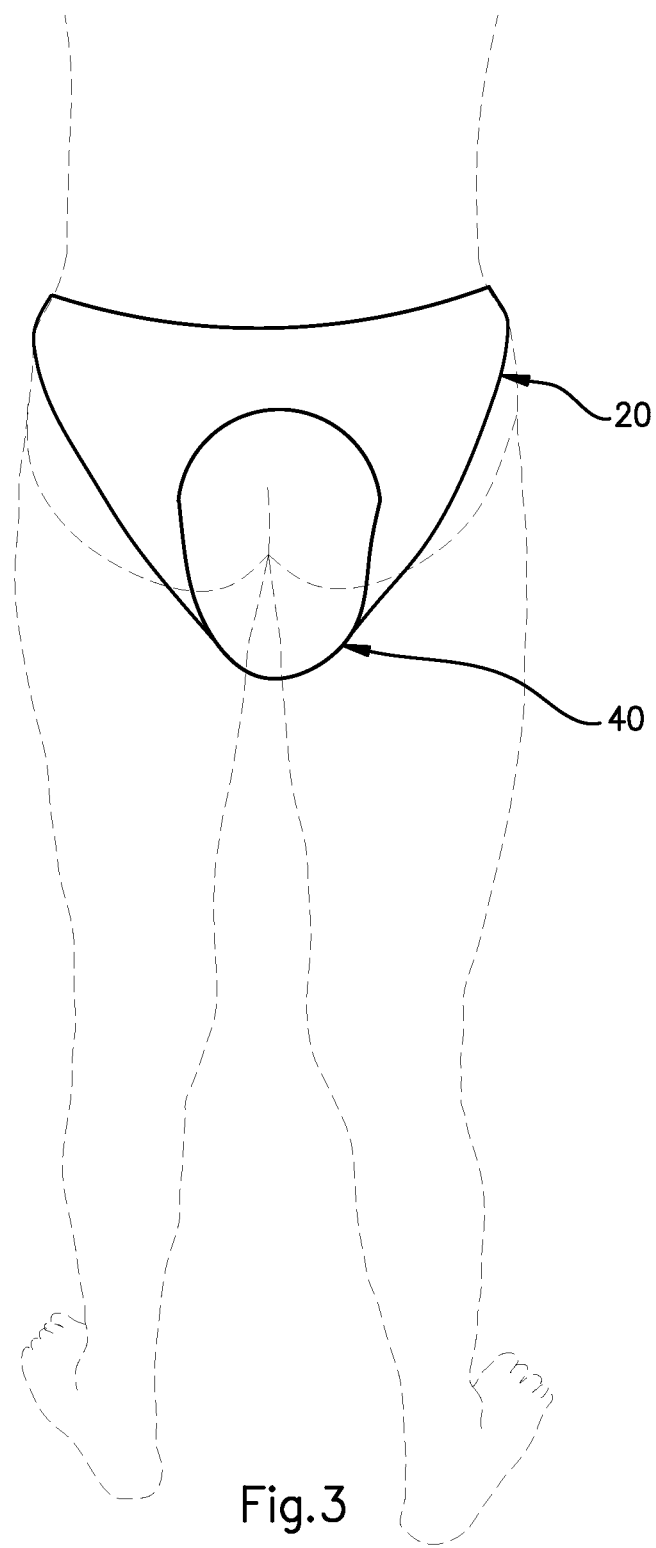
FIG. 3 illustrates the rear elevational view of the present invention fastened on to a user.
Figure 4:
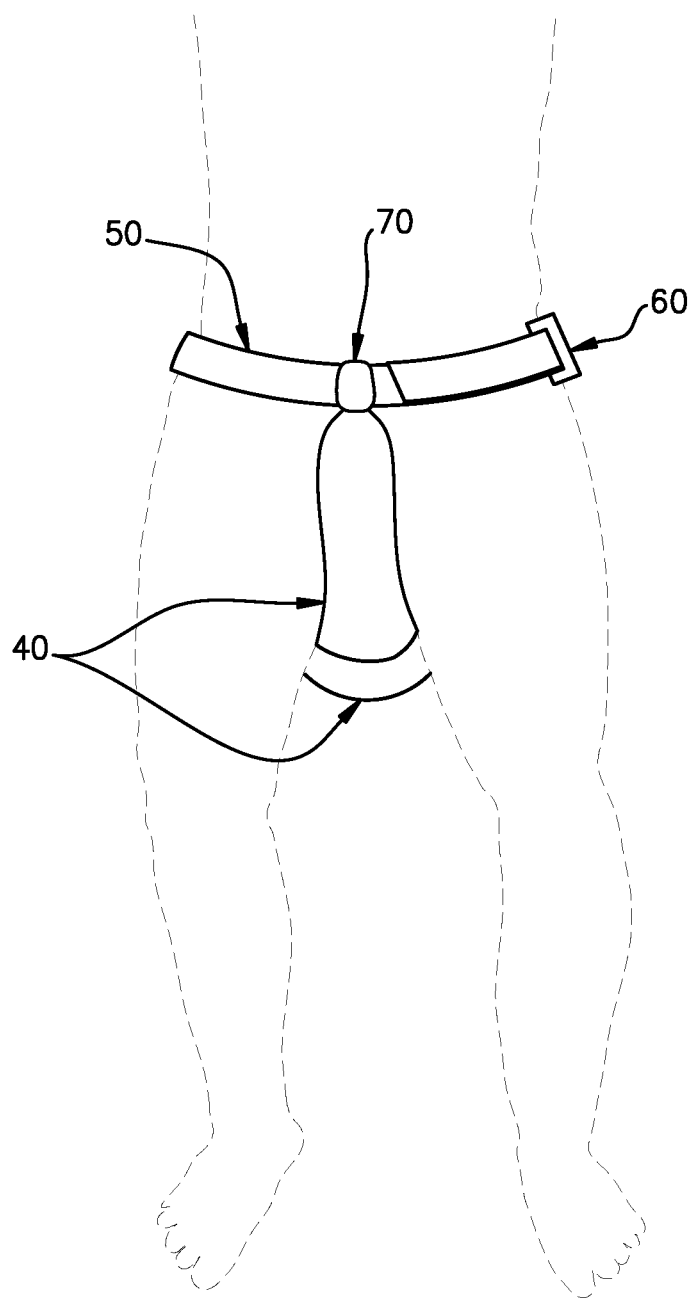
FIG. 4 illustrates the front elevational view of the present invention fastened on to a user.

Referring now to the drawings, where the present invention is generally referred to with numeral 10, it can be observed that it basically includes a flexible sheet 20, rim assembly 30, reservoir assembly 40, belt assembly 50, belt buckle assembly 60, and loop assembly 70. While the inventor refers to the different elements that comprise her invention as assemblies, to the extent that is feasible, these assemblies are intended to be part of a unitary piece using molding, thermosetting, or equivalent techniques compatible with production concerns.

Sheet assembly 20 has a substantially triangular shape and is made out of a liquid impermeable material. Sheet assembly 20 has two lateral ends 21 and 21' defining rear side 22' in between. Belt assembly 50 and buckle assembly 60 are, respectively, attached or extent from ends 21 and 21'. End 22 of sheet assembly 20 is opposite to the side 22' defined between ends 21 and 21'.

Rim assembly 30 is slightly stiffer than sheet assembly 20 but is still flexible. It can be part of sheet assembly 20 with an added reinforcement, in one of the preferred embodiments. Rim assembly 30 includes two portions, enlarged portion 34 and relatively narrow portion 36, which extend longitudinally terminating with front end 22. Loop 70 extends forward from the end 22 of assembly 30. Rear side 22' is wider than front side 22. Rim assembly 30 can include, in one of the preferred embodiments, an adhesive substance 33 to permit its sealing, as seen in FIG. 5. Adhesive substance 33 can be protected with sealable film 31.

Belt assembly 50, having ends 51 and 51', includes a belt 52 with pressure sensitive adhesive pads 54 and 56 at its end 51. End 51 of belt assembly 50 includes a piece of pressure sensitive adhesive member 54 that removably attaches to mating pad 56 of pressure sensitive adhesive material in one of the preferred embodiments. There are many belt and buckle mechanisms that are equivalent. End 51 of belt 52 is passed through loop 70 to support end 22 of the waste bag while it is being worn, allowing any expelled fluids to be directed towards reservoir 40. End 51 of belt 52 continues around the waist and is pulled through loop 60 so that pressure sensitive pad 54 can be mated with pad 56 to allow a user to tighten the belt around a user's waist. In an alternate embodiment loop 60 can be replaced by mating pad 56 allowing the device to be worn with a belt of predetermined length.

The present invention, when in use, is designed to attach to the wearer by means of rim 32, which is pressure fit to the groin area to encase the genitals in reservoir portion 40. Narrow portion 36 has a cooperative shape to direct the flow of urine to enlarged reservoir portion 34. Reservoir portion 40 is a flexible material that attaches to rim 32 and can be compressed within rim 32 to become volumetrically efficient defining a relatively flat surface for storage and transportation.

As shown in FIGS. 5, 6, and 7, after use it is easy to dispose of the waste bag. Rim assembly 30 is, in the preferred embodiment described here, longitudinally symmetrical and can be folded accordingly. The adhesive will substantially seal the contents. Layers of absorbed material, like those used in baby diapers, can be added, if desired. A user can readily wrap the bag and discard it.

A preferably biodegradable pad can be mounted to the inside of reservoir portion 40 to absorb urine and fecal matter. Also, the use of fragrances can be used.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A disposable waste bag, comprising:
   A) a flexible and impermeable sheet having substantially a truncated triangular shape defining a front end and an opposite rear side with first and second lateral rear ends;
   B) an elongated flexible rim member having a narrow portion and an enlarged portion, said narrow portion starting from said front end and extending longitudinally towards said rear side having cooperative ergonomic dimensions to surround the genital area and said enlarged portion extending longitudinally from said narrow portion and having cooperative ergonomic dimensions to surround the perianal area, and said enlarged portion being adjacent to said sheet and said rim member further including adhesive means for sealing said rim against the body of user;
   C) a loop assembly mounted to said front end;
   D) belt means having first and second ends, said first end being mounted to said first lateral rear end and said second end being selectively passed through said loop assembly and removably attached to said second lateral rear end and said belt means being positioned around a user's waist so that said belt means keeps said disposable waste bag in place.

2. The disposable waste bag set forth in claim 1, wherein said second lateral end includes buckle means for receiving said first end.

3. The disposable waste bag set forth in claim 2 wherein said first end includes first and second mating pressure sensitive adhesive means.

4. The disposable waste bag set forth in claim 3 wherein said rim member extends symmetrically and longitudinally from said front end to said rear side.

5. The disposable waste bag set forth in claim 4 wherein said sheet, rim member, belt means and loop assembly are made of a unitary flexible material.

6. The disposable waste bag set forth in claim 5 made out of a biodegradable material.

\* \* \* \* \*